United States Patent [19]

Hillstead

[11] Patent Number: 4,885,003
[45] Date of Patent: Dec. 5, 1989

[54] DOUBLE MESH BALLOON CATHETER DEVICE

[75] Inventor: Richard A. Hillstead, Hollywood, Fla.

[73] Assignee: Cordis Corporation, Miami, Fla.

[21] Appl. No.: 223,869

[22] Filed: Jul. 25, 1988

[51] Int. Cl.$^4$ .............................................. A61B 17/32
[52] U.S. Cl. ...................................... 604/22; 604/107; 128/305; 128/344
[58] Field of Search .............................. 604/104–107, 604/95, 96, 22, 268; 128/344, 341–343, 325

[56] References Cited

U.S. PATENT DOCUMENTS

| 2,498,692 | 2/1950 | Mains | 128/348 |
|---|---|---|---|
| 2,816,552 | 12/1957 | Hoffman | 128/305 |
| 3,416,531 | 12/1968 | Edwards | 128/348 |
| 3,495,586 | 2/1970 | Regenbogen | 128/6 |
| 3,568,659 | 3/1971 | Karnegia | 128/1 |
| 3,692,029 | 9/1972 | Adair | 128/349 R |
| 3,713,447 | 1/1973 | Adair | 128/347 |
| 3,938,530 | 2/1976 | Santomieri | 128/349 R |
| 3,996,938 | 12/1976 | Clark, III | 128/348 |
| 4,154,242 | 5/1979 | Termanini | 128/349 R |
| 4,535,757 | 8/1985 | Webster, Jr. | 128/1 D |
| 4,572,186 | 2/1986 | Gould et al. | 128/341 |
| 4,608,965 | 9/1986 | Anspach, Jr. et al. | 128/4 |
| 4,650,466 | 3/1987 | Luther | 604/95 |
| 4,655,745 | 4/1987 | Corbett | 604/49 |
| 4,693,243 | 9/1987 | Buras | 128/207 |
| 4,706,670 | 11/1987 | Andersen et al. | 128/344 |
| 4,790,812 | 12/1988 | Hawkins et al. | 604/22 |

Primary Examiner—Stephen C. Pellegrino
Attorney, Agent, or Firm—Henry W. Collins; Thomas R. Vigil

[57] ABSTRACT

The double mesh balloon catheter device comprises a catheter having a proximal end and a distal end, a double tubular mesh assembly having a proximal end and a distal end, being mounted to the distal end of the catheter and having an outer tubular mesh and an inner tubular mesh. An actuating mechanism is coupled to the proximal end of the catheter and extends through the catheter to the double tubular mesh assembly for moving the distal end thereof to effect axial contraction of the double tubular mesh assembly. Another actuating mechanism is coupled to the proximal end of the catheter and extends through the catheter to the double tubular mesh assembly for causing rotation of the inner tubular mesh relative to the outer tubular mesh.

25 Claims, 1 Drawing Sheet

U.S. Patent    Dec. 5, 1989    4,885,003
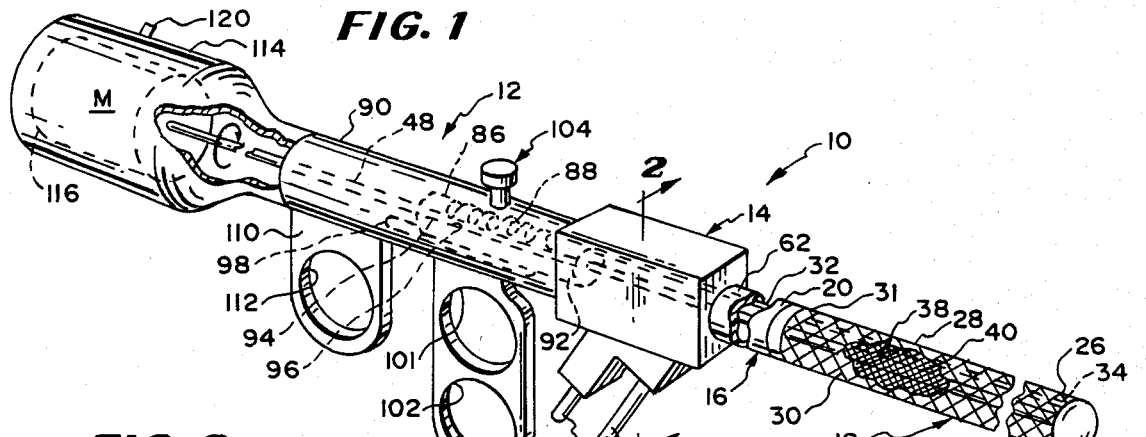
FIG. 1
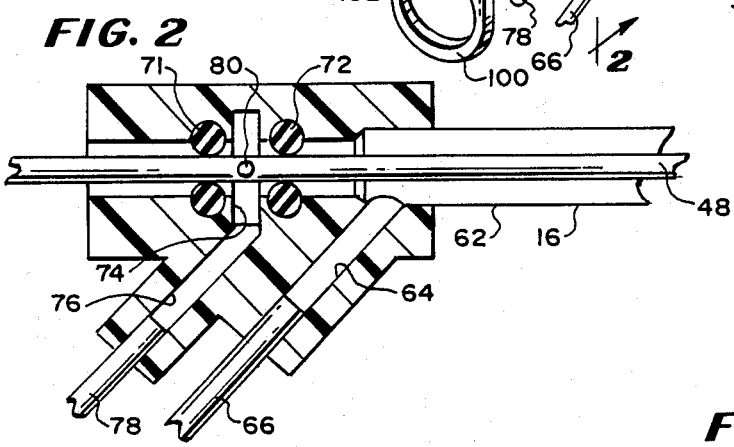
FIG. 2
FIG. 3
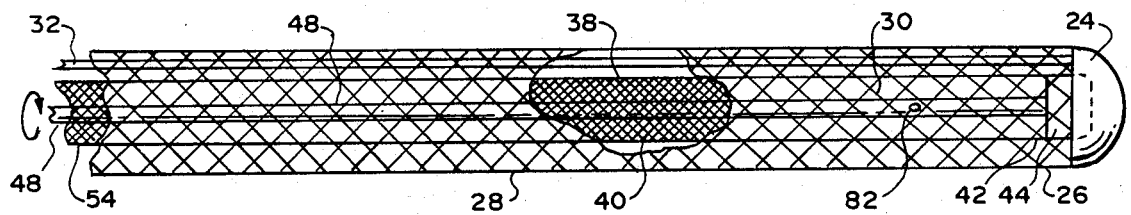
FIG. 4
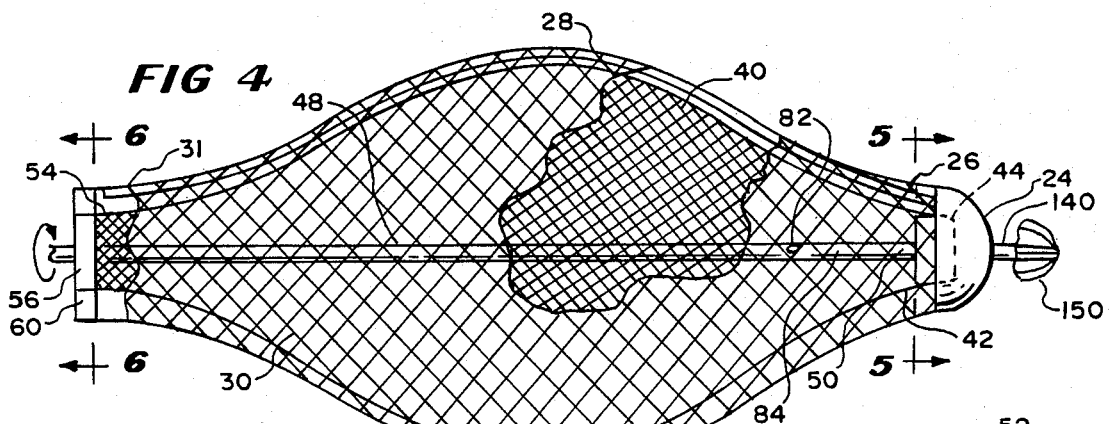
FIG. 6
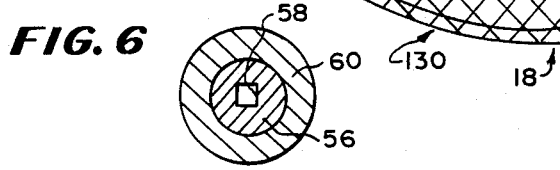
FIG. 5
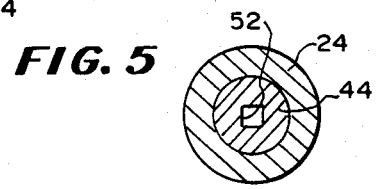

DOUBLE MESH BALLOON CATHETER DEVICE

BACKGROUND OF THE INVENTION

1. Field of the Invention

The present invention relates to a double mesh balloon catheter device which can be used to expand and remove the buildup of material in a vessel, such as the buildup of plaque in an area of stenosis in a blood vessel.

2. Description of the Prior Art

Heretofore it has been proposed to provide an angioplasty device having a flexible woven tube which can be contracted axially to cause the woven tube to balloon outwardly to form a mesh balloon in the Luther U.S. Pat. No. 4,650,466.

The Luther patent teaches the construction of such an angioplasty device in the form of a woven tube of tubular fabric mounted forwardly of a catheter and having a guidewire arrangement for retracting the distal end of the tubular fabric relative to the proximal end thereof. The woven tube may be lined with a filter cloth of nylon or polyester which expands with the woven tube for collecting particles and debris and for removing same from a vessel.

As will be described in greater detail hereinafter, the double mesh balloon catheter device of the present invention differs from the angioplasty device disclosed in the Luther patent by providing a double tubular mesh assembly including an inner tubular mesh and an outer tubular mesh. Both tubular meshes can be axially contracted together to create a double mesh balloon and a mechanism is provided for rotating the inner tubular mesh within the outer tubular mesh to shave off plaque material extending through both meshes.

SUMMARY OF THE INVENTION

According to the invention there is provided a double mesh balloon catheter device comprising:

a catheter having a proximal end and a distal end;

a double tubular mesh assembly having a proximal end and a distal end, being mounted to the distal end of said catheter and having an outer tubular mesh and an inner tubular mesh; and actuating means coupled to the proximal end of the catheter and extending through the catheter to the double tubular mesh assembly for moving the distal end thereof to effect axial contraction of the double tubular mesh assembly.

Further according to the invention there is provided a double mesh balloon catheter device comprising:

a catheter having a proximal end and a distal end;

a double tubular mesh assembly having a proximal end and a distal end, being mounted to the distal end of said catheter and having an outer tubular mesh and an inner tubular mesh; and actuating means coupled to the proximal end of the catheter and extending through the catheter to the double tubular mesh assembly for causing rotation of the inner tubular mesh relative to the outer tubular mesh.

BRIEF DESCRIPTION OF THE DRAWINGS

FIG. 1 is a perspective view of a double mesh balloon catheter device constructed according to the teachings of the present invention.

FIG. 2 is a cross-section of a Luer fitting connected between the proximal end of the catheter of the device and an actuating handle mechanism of the device for controlling operation of the double mesh balloon device.

FIG. 3 is an enlarged view of the double tubular mesh assembly located in the distal end portion of the device.

FIG. 4 is an enlarged longitudinal plan view with portions broken away of the double tubular mesh assembly located in the distal end portion of the device shown in FIG. 1 with the distal ends of the tubular meshes moved rearwardly relative to the proximal end of the tubular meshes so as to cause the tubular meshes to expand laterally outwardly to form a balloon.

FIG. 5 is a sectional view taken along lines 5—5 of FIG. 4 and shows a spline connection of a central flush tube to a distal bearing in a distal cap member at the distal end of the device shown in FIG. 1.

FIG. 6 is a sectional view through a collar at the distal end of the catheter of the device showing a similar spline connection between the flush tube and a proximal bearing.

DESCRIPTION OF THE PREFERRED EMBODIMENT

Referring now to the drawings in greater detail, there is illustrated in FIG. 1 a double mesh balloon device 10 constructed according to the teachings of the present invention. The device 10 includes an actuating handle mechanism 12, a Luer TM fitting 14, a catheter 16 which is shown broken to indicate that it is much longer than as shown in FIG. 1, and a double tubular mesh assembly 18 connected to a distal end 20 of the catheter 16.

Starting from a distal end 22 of the device 10 and with reference to FIGS. 1, 3, 4 and 5, there is located at the distal end 22 a cap member 24. Fixed to the cap member 24 is a distal end 26 of an outer tubular mesh 28. The outer tubular mesh 28 is a woven tube of interlaced filaments 30. The filaments 30 can be made of a plastic material or a metal such as stainless steel. A proximal end 31 of the outer tubular mesh is fixed to the distal end 20 of the catheter 16.

Connected to the cap member 24 within the outer tubular mesh 28 is a control wire 32, shown in FIG. 3, which has a distal end 34 connected to the cap member 24 and which extends slidably through the catheter 16.

The double tubular mesh assembly 18 further includes an inner tubular mesh 38 formed from a tube of woven interlaced filaments 40 that can be made of plastic or metal material. The inner tubular mesh 38 is shown as having a smaller mesh size than the outer tubular mesh 38. However, preferably the inner tubular mesh 38 will have a mesh size which is approximately the same mesh size as the mesh size of the outer tubular mesh 28.

A distal end 42 of the inner tubular mesh 38 is fixed to a bearing 44 which is rotatably mounted within the cap member 24.

A flush tube 48 has a distal end 50 thereof fixed within the bearing 44 such as by means of a square spline formation received in a square splined opening 52 in the bearing 44 as shown in FIG. 5.

With this construction, rotation of the flush tube 48 will cause rotation of the inner tubular mesh 38 relative to the outer tubular mesh 28. Also, it is to be understood that the control wire 32 can, if desired, be situated within the inner tubular mesh 38 and fixed to the bearing 44 and then will be rotatable with the flush tube 48.

As best shown in FIG. 4, a proximal end 54 of the inner tubular mesh 38 is fixed to a bearing 56 which can have a spline bore 58 therethrough as shown in FIG. 4, or which can have a circular bore therethrough. The spline bore 58 is preferred, since such a spline connection with a mating spline formation on the flush tube 48 ensures that the proximal and distal ends 54 and 42 of the inner tubular mesh 38 are rotated together to rotate the inner tubular mesh 38 within the outer tubular mesh 28 without twisting of the inner tubular mesh 38.

The bearing 56 is mounted in a collar 60 which is fixed to the distal end 20 of the catheter 16 shown in FIG. 1.

If desired, to prevent twisting of the flush tube 48, the flush tube 48 can be constructed as a layered tube including an inner plastic extruded tube, a braided mesh tube of material on the outer surface of the inner tube and then an outer tube or coating of plastic material over the braided mesh. Such a nontwisting torque transmitting catheter is sold under the trademark Ducor and can be of the type disclosed in the Stevens U.S. Pat. No. 3,585,707, the disclosure of which is incorporated herein by reference.

The catheter 16 extends for some distance from the collar 60 to a proximal end 62 thereof which is connected to the Luer TM fitting 14. Within the Luer TM fitting 14 is a side port 64 (FIG. 2) to which a drainage tubing 66 can be attached and which communicates with the interior of the catheter 14 for draining fluid from the area within the double tubular mesh assembly 18 through the catheter 16 and out through the drainage tubing 66 shown in FIG. 2. Then, the inner flush tube 48 extends within the Luer TM fitting 14 through a pair of spaced apart 0 rings 71, 72 which are spaced on either side of an annular area 74 within the Luer TM fitting 14 which is connected to another side port 76 to which a flush tubing 78 can be connected.

The flush tube 48 has a hole 80 therein in the area thereof between the two 0 rings 71 and 72. The flush tube 48 also has a hole 82 in a distal end portion 84 thereof as shown in FIGS. 3 and 4 through which flushing fluid is ejected into the double tubular mesh assembly 18.

The flush tube 48 extends rearwardly through the actuating handle mechanism 12 which includes an elongate rod like member 86 which has a ratchet formation 88 on the upper side thereof and which is received in a cylinder 90 forming part of the actuating handle mechanism 12. The control wire 32 is fixed to a distal end 92 of this rod like member 86 as shown in FIG. 1.

Alternatively, the control wire 32 can be eliminated and a portion 94 of the flush tube 48 received within and through a central bore 96 in the rod like member 86 can be rotatably received within the rod like member 86 for rotation therein, but with some means for restraining axial movement of the flush tube 48 relative to the rod like member 86. This can be achieved by providing annular grooves within the rod like member 86 and disks or rings fixed on the flush tube 48 and positioned within the rod like member 86 and received in the annular grooves, or a disk on the flush tube 48 adjacent each end of the rod like member 86, so that the flush tube 48 can rotate within the bore 96 in the rod like member 86 but will move rearwardly or forwardly with the rod like member 86 when it is moved.

This construction may be preferred to eliminate the control wire 32 and yet provide for two mechanical operations, one being movement of the cap member 24 rearwardly relative to the collar 60 to expand the two tubular meshes 28 and 38 as shown in FIG. 4 and yet permit rotation of the flush tube 48 to rotate the inner tubular mesh 38 relative to the outer tubular mesh 228.

The handle actuating mechanism 12 further includes a slot 98 in the bottom of the cylinder 90 from which a plate like trigger member 100 having two finger holes 101 and 102 extends and which is fixed to the lower side of the rod like member 86 and is engaged by two fingers for moving the rod like member 86 rearwardly (or forwardly). A ratchet pin 104 is mounted in a hole in an upper surface of the cylinder 90 and engages the ratchet formation 88 on the rod like member 86 such that the rod like member 86 can be moved rearwardly or "ratcheted" relative to the ratchet pin 104. The pin 104 holds the rod like member 86 in a predetermined position depending upon which notch of the ratchet formation 88 the inner end (not shown) of the ratchet pin 104 is received.

Depending from the rear lower side of the cylinder 90 of the actuating handle mechanism 12 is a short plate-like member 110 having a finger hole 112 therein for receiving a thumb.

Then, connected to the rear or proximal end of the cylinder 90 is a housing 114 for mounting a motor 116 which has an output shaft coupled to a proximal end 118 of the flush tube 48. An actuating switch 120 is preferably mounted on the outer surface of the housing 114 and can be actuated by the other hand of the physician using the double mesh balloon catheter device 10. This switch 120 can be an on/off switch or it can be an on/off switch combined with a variable current switch of the type which includes an SCR motor speed control circuit whereby the speed of rotation of the flush tube 48 can be varied as desired.

The position of the platelike trigger member 100 relative to the short plate like member 110 indicates the amount of expansion of the double mesh balloon assembly 18 at the distal end of the double mesh balloon catheter device 10.

Also, it is to be understood that the Luer TM fitting 14 can be positioned forwardly of the actuating handle mechanism 12 rather than being mounted adjacent the actuating handle mechanism 12, as shown in FIG. 1.

In the use of the double mesh balloon catheter device 10 of the present invention, a physician will first insert the catheter 16 and double tubular mesh assembly 18 at the distal end thereof into a vessel or body cavity, such as a blood vessel, until the double tubular mesh assembly 18 is located in a desired position such as at the position of an area of stenosis caused by plaque buildup within a blood vessel.

Once the double tubular mesh assembly 18 is located in a desired position, the physician will pull the trigger member 100 rearwardly to cause the double tubular mesh assembly 18 to expand transversely outwardly to a balloon shape 130, as shown in FIG. 4.

Next, the physician will activate the flushing system for supplying a flushing liquid through the tubing 78, the side port 76, the annular space 74 within the Luer TM fitting 14, hole 80 and through the flush tube 48 to the hole 82 in the outer end portion 84 thereof. Then if desired, the physician can connect the drainage tubing 66 from the drainage port 64 connected to the interior of the catheter 16 to a drainage, suction or evacuation device for ensuring evacuation of debris and liquid from the area within the tubular meshes 38 and 48.

Finally, in order to remove the buildup of material, such as plaque material, in the area of stenosis, the physician will activate the switch 120 to cause the motor 116 to rotate thereby to rotate the inner tubular mesh 38 in its expanded state as shown in FIG. 4 within the outer tubular mesh 28 thereby to "shave" or cut off pieces of plaque or other material extending through the screen or mesh of the contracted outer tubular mesh 28 and the inner tubular mesh 38.

The double mesh balloon device 10 of the present invention can be placed in an occluded area in a vessel, such as an area of stenosis in a blood vessel, and can be actuated to cut away, flush and evacuate material from the occluded area in a simple and efficient manner.

From the foregoing description, it will be apparent that the double mesh balloon catheter device 10 of the present invention has a number of advantages some of which have been described above and other of which are inherent in the invention. In this respect, it will be appreciated that the rotation of the inner tubular mesh 38 relative to the outer tubular mesh 28 functions very much like an electric shaver for the purpose of shaving off particles of plaque that extend through the outer tubular mesh 28 and the inner tubular mesh 38.

Also, from the foregoing description, it will be apparent that modifications can be made to the double mesh balloon catheter device 10 of the present invention without departing from the teachings of the invention. For example, a distal end 140 of the flush tube 48 can extend beyond the cap member 24 and have a cutting element 150 mounted thereon, as shown in FIG. 4, such cutting element 150 enabling the double mesh balloon catheter device 10 to cut through an occluded area to provide enough space for receiving the double tubular mesh assembly of the device therein for "shaving" occluded material in the occluded area of the vessel.

The double tube mesh assembly 18 can be heated by means of electrical induction, radio frequency energy or fiberoptic laser light, using an electrical circuit including wire conductors 171 and 172 or using a fiber optic 173 shown in FIG. 4.

In view of the modifications that can be made to the device 10 of the present invention, some of which have been described above, the scope of the invention is only to be limited as necessitated by the accompanying claims.

I claim:

1. A double mesh balloon catheter device comprising:
   a catheter having a proximal end and a distal end;
   a double tubular mesh assembly having a proximal end and a distal end, being mounted to the distal end of said catheter and comprising an outer tubular mesh and an inner tubular mesh; and
   actuating means coupled to the proximal end of the catheter and extending thorough the catheter to the double tubular mesh assembly for moving the distal end thereof to effect axial contraction of the double tubular mesh assembly.

2. The device of claim 1 wherein said actuating means comprises a control wire extending axially through said double tubular mesh assembly and said catheter and an actuating mechanism coupled to the proximal end of said catheter, said control wire having a proximal end coupled to said actuating mechanism and a distal end connected to the distal end of said double tubular mesh assembly.

3. The device of claim 1 includes further actuating means comprising an elongate member within said catheter and said double tubular mesh assembly and fixed to the distal end of said double tubular mesh assembly and a further actuating mechanism coupled to the proximal end of said catheter and having a proximal end of said elongate member coupled thereto.

4. The device of claim 3 wherein said elongate member is a flush tube which is connected to the distal end of said double tubular mesh assembly, which has a side hole therein opening into the double tubular mesh assembly and which is coupled at its proximal end to a source of flushing fluid.

5. The device of claim 3 wherein said double tubular mesh assembly includes an end cap to which the distal end of said outer tubular mesh is connected, a bearing rotatably mounted in said end cap, said elongate member being coupled to said bearing, and means at the proximal end of said device coupled to said elongate member for rotating same to rotate said inner tubular mesh within said outer tubular mesh.

6. The device of claim 5 wherein said bearing has a spline opening therein and the distal end of said elongate member has a spline formation received and fixed within said spline opening in said bearing.

7. The device of claim 5 wherein said elongate member is hollow so as to form a flush tube and has a side hole in the distal end portion thereof for ejecting flushing fluid into the double tubular mesh assembly.

8. The device of claim 7 including means for rotatably mounting a proximal end portion of said flush tube and means for supplying flushing liquid to said rotatably mounted proximal end portion of said flush tube.

9. The device of claim 5 wherein said elongate member extends through said cap member and a cutting element is mounted to the distal end of said elongate member extending forwardly of said double tubular mesh assembly.

10. The device of claim 3 including a collar at the distal end of said catheter to which the proximal end of said outer tubular mesh is connected, a bearing mounted in said collar and said elongate member extending slidably through said bearing.

11. The device of claim 10 wherein said elongate member has a spline formation thereon which extends through a mating spline opening in said bearing mounted in said collar.

12. The device of claim 1 including means for connecting a drainage tube to the proximal end of said catheter whereby debris and fluid entering into the double mesh assembly can be withdrawn or evacuated through said catheter and said drainage tube.

13. A double mesh balloon catheter device comprising:
   a catheter having a proximal end and a distal end;
   a double tubular mesh assembly having a proximal end and a distal end, being mounted to the distal end of said catheter and having an outer tubular mesh and an inner tubular mesh rotatably journaled within said outer tubular mesh; and
   actuating means coupled to the proximal end of the catheter and including means extending through the catheter to the double tubular mesh assembly and connected to said inner tubular mesh, said actuating means being operable for causing rotation of the inner tubular mesh relative to the outer tubular mesh.

14. The device of claim 13 wherein said actuating means includes an elongate member within said catheter and said tubular mesh assembly and rotatably journaled to the distal end of said double tubular mesh assembly and an actuating mechanism coupled to the proximal end of said catheter and connected to the proximal end of said elongate member for rotating said elongate member to rotate said inner tubular mesh within said outer tubular mesh.

15. The device of claim 14 wherein said double tubular mesh assembly includes an end cap to which the distal end of said outer tubular mesh is connected, a bearing rotatably mounted in said end cap, said elongate member being coupled to said bearing.

16. The device of claim 15 wherein said bearing has a spline opening therein and the distal end of said elongate member has a spline formation received and fixed within said spline opening in said bearing.

17. The device of claim 15 wherein said elongate member is hollow so as to form a flush tube and has a side hole in the distal en portion thereof for ejecting flushing fluid into the double tubular mesh assembly.

18. The device of claim 17 including means for rotatably mounting a proximal end portion of said flush tube and means for supplying flushing liquid to said rotatably mounted proximal end portion of said flush tube.

19. The device of claim 15 wherein said elongate member extends through said cap member and a cutting element is mounted to the distal end of said elongate member extending forwardly of said double tubular mesh assembly.

20. The device of claim 13 including a collar at the distal end of said catheter to which the proximal end of said outer tubular mesh is connected, a bearing mounted in said collar and said elongate member extending slidably through said bearing.

21. The device of claim 20 wherein said elongate member has a spline formation thereon which extends through a mating spline opening in said bearing mounted in said collar.

22. The device of claim 13 including means for connecting a drainage tube to the proximal end of said catheter whereby debris and fluid entering into the double mesh assembly can be withdrawn or evacuated through said catheter and said drainage tube.

23. The device of claim 13 including said actuating means coupled to the proximal end of the catheter and extending through the catheter to the double tubular mesh assembly for moving the distal end thereof to effect axial contraction of the double tubular mesh assembly.

24. The device of claim 13 including means located at said double tubular mesh assembly for heating the outer mesh.

25. The device of claim 13 including means located at said double tubular mesh assembly for heating the inner mesh.

* * * * *